United States Patent
Cho

(10) Patent No.: US 9,682,182 B2
(45) Date of Patent: Jun. 20, 2017

(54) DIALYSATE SUPPLY UNIT AND BLOOD DIALYZING APPARATUS HAVING THE SAME

(71) Applicant: Taebeom Cho, Dáejeon (KR)

(72) Inventor: Taebeom Cho, Dáejeon (KR)

(73) Assignee: HUMAN BIOMED, INC

( * ) Notice: Subject to any disclaimer, the term of this patent is extended or adjusted under 35 U.S.C. 154(b) by 352 days.

(21) Appl. No.: 14/243,943

(22) Filed: Apr. 3, 2014

(65) Prior Publication Data
US 2015/0283314 A1  Oct. 8, 2015

(51) Int. Cl.
*A61M 1/14* (2006.01)
*A61M 1/16* (2006.01)

(52) U.S. Cl.
CPC .................................. *A61M 1/1649* (2014.02)

(58) Field of Classification Search
CPC .......................... A61M 1/1645; A61M 1/1694
See application file for complete search history.

(56) References Cited

U.S. PATENT DOCUMENTS

| | | | |
|---|---|---|---|
| 4,857,199 A * | 8/1989 | Cortial | A61M 1/16 210/101 |
| 4,935,125 A | 6/1990 | Era et al. | |
| 5,466,228 A * | 11/1995 | Evans | F16K 11/0853 137/625.47 |
| 2009/0062741 A1* | 3/2009 | Smith | A61M 5/19 604/191 |
| 2009/0187138 A1* | 7/2009 | Lundtveit | A61M 1/16 604/29 |

FOREIGN PATENT DOCUMENTS

| | | |
|---|---|---|
| KR | 10-2004-0026193 | 3/2004 |
| KR | 10-2011-0088438 | 8/2011 |
| KR | 10-2013-0124039 | 11/2013 |
| KR | 10-1349221 | 2/2014 |

* cited by examiner

*Primary Examiner* — Krishnan S Menon
*Assistant Examiner* — Ryan B Huang
(74) *Attorney, Agent, or Firm* — Lee Global Patent, LLC

(57) ABSTRACT

Provided is a dialysate supply unit and a blood dialyzing apparatus including the dialysate supply unit for supplying dialysate of a dialysate tank to a hemodialyzer and collecting dialysate passing through the hemodialyzer in an effluent tank. The dialysate supply unit includes a dialysate pump, an effluent pump, a first flow-blocking valve, a second flow-blocking valve, and a flow-blocking valve driver. The dialysate pump connects the dialysate tank and the hemodialyzer and the effluent pump connects the hemodialyzer and the effluent tank. The first flow-blocking valve alternately blocks a dialysate outflow tube connecting the hemodialyzer and the dialysate pump and an effluent inflow tube connecting the hemodialyzer and the effluent pump. The second flow-blocking valve alternately blocks a dialysate inflow tube connecting the dialysate pump and the dialysate tank and an effluent outflow tube connecting the effluent pump and the effluent tank. The flow-blocking valve driver drives the flow-blocking valve.

10 Claims, 11 Drawing Sheets

FIG.9
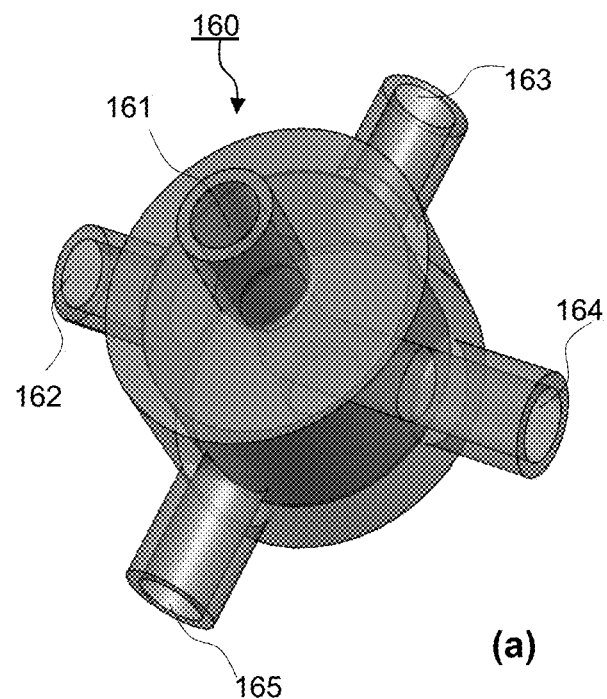
(a)
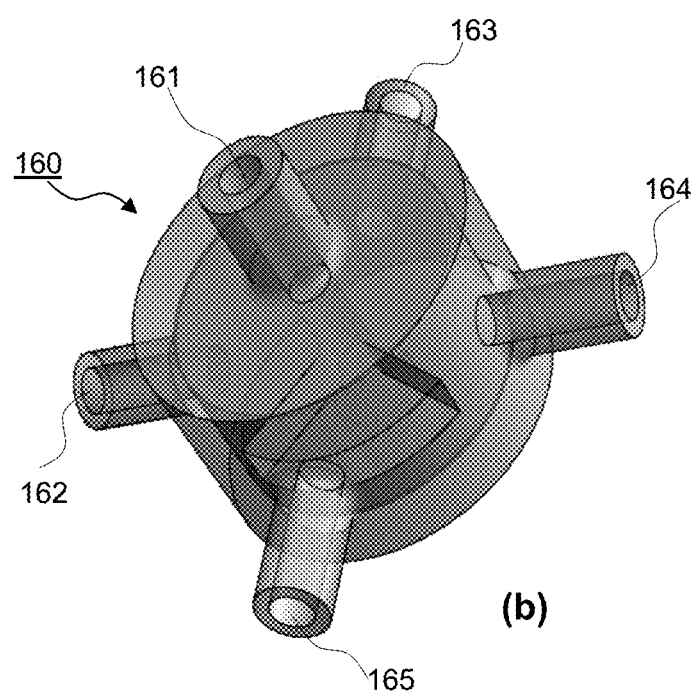
(b)

DIALYSATE SUPPLY UNIT AND BLOOD DIALYZING APPARATUS HAVING THE SAME

BACKGROUND OF THE INVENTION

The present invention relates to a dialysate supply unit and a blood dialyzing apparatus including the dialysate supply unit, and more particularly, to a dialysate supply unit, which is configured to improve water exchange and mass transfer between blood and dialysate by quickly changing the dialysate pressure in a hemodialyzer using a pulsatile dialysate flow.

When there is a kidney dysfunction, water and waste products that have to be discharged out of body accumulate in blood and imbalance of electrolytes in the body occurs. Most commonly performed to improve such a kidney failure symptom, is hemodialysis which is to circulate blood out of body and rid the blood of the accumulated uremic toxin and excess water by a semi-permeable dialysis membrane. Hemodialysis is a method of seeking an electrolyte balance and ridding the body fluid of uremic toxin and excess water, taking advantages of diffusion applied due to the concentration difference and filtration applied due to the pressure difference between blood and dialysate. Most commonly used of hemodialyzer is the type that is a cylinder-shape container charged with a bundle of hollow fiber membranes and port-processed at both ends thereof by use of a synthetic resin like polyurethane. It is because the hollow fiber hemodialyzer has excellent mass-transfer efficiency resulting from large effective surface area between blood and dialysate compared to the small size as a whole.

A hemodialysis apparatus includes a hemodialyzer, a blood pump designed to supply a patient's blood to the hemodialyzer, a dialysate supply unit that supplies or discharges dialysate. Blood and dialysate each decrease their hydrostatic pressure while passing through a hemodialyzer. Since blood and dialysate flow in opposite directions inside the hemodialyzer, a filtration occurs at the proximal part of the hemodialyzer such that water in the blood moves toward dialysate compartment because blood pressure is higher than dialysate pressure, while a backfiltration occurs at the distal part such that water in the dialysate moves toward blood domain for the same reason. When a filtration takes place, wastes in blood are also eliminated, which is referred to as a convective mass transfer. It is known that uremic toxins of medium molecular size are efficiently removed by the convective mass transfer and thus dialysis efficiency and prognosis on patients have greatly improved. However, there is a big hurdle in the effort to improve dialysis efficiency by the convective mass transfer, because hemodialyzers in typical hemodialysis apparatuses are limited in size and blood flow rate is restrictively allowed to be increased in consideration of the weight and blood vessel condition of a patient.

SUMMARY OF THE INVENTION

The present invention provides a dialysate supply unit and a blood dialyzing apparatus including the dialysate supply unit, which can improve the hemodialysis efficiency by allowing a pressure difference between blood and dialysate to be alternately changed into positive and negative values without increasing the size of a hemodialyzer or the blood flow rate.

Embodiments of the present invention provide dialysate supply units for supplying dialysate of a dialysate tank to a hemodialyzer and collecting dialysate passing through the hemodialyzer, i.e., effluent, in an effluent tank, the dialysate supply unit including: a dialysate pump connecting the dialysate tank and the hemodialyzer; an effluent pump connecting the hemodialyzer and the effluent tank; a first flow-blocking valve alternately blocking a dialysate outflow tube connecting the hemodialyzer and the dialysate pump and an effluent inflow tube connecting the hemodialyzer and the effluent pump; a second flow-blocking valve alternately blocking a dialysate inflow tube connecting the dialysate pump and the dialysate tank and an effluent outflow tube connecting the effluent pump and the effluent tank; and a flow-blocking valve driver for driving the flow-blocking valves. The dialysate and effluent pumps are composed of a cylinder having an internal space, a piston reciprocally disposed inside the cylinder, and a piston driver allowing the piston to reciprocate.

When the dialysate pump cylinder is expanded, dialysate of the dialysate tank flows into the dialysate pump cylinder. On the other hand, when the dialysate pump cylinder is compressed, dialysate of the cylinder is discharged to the hemodialyzer. Similarly, when the effluent pump cylinder is expanded, effluent flows into the effluent pump cylinder, and when the effluent pump cylinder is compressed, effluent in the cylinder is discharged to the effluent tank. In the dialysate supply unit, the piston driver may simultaneously compress or expand the dialysate and the effluent pump cylinders. When the dialysate and effluent pump cylinders are compressed, the first flow-blocking valve opens the dialysate outflow tube and blocks the effluent inflow tube, and the second flow-blocking valve opens the effluent outflow tube and blocks the dialysate inflow tube. On the other hand, when the dialysate and effluent pump cylinders are expanded, the first flow-blocking valve opens the effluent inflow tube and blocks the dialysate outflow tube, and the second flow-blocking valve opens the dialysate inflow tube and blocks the effluent outflow tube.

A blood dialyzing apparatus may include a hemodialyzer in which a mass transfer occurs between blood and dialysate, a blood tube connecting between the hemodialyzer and a patient, a blood pump disposed on the blood tube to transfer blood, a dialysate tank storing dialysate, an effluent tank collecting effluent passing through the hemodialyzer, and a dialysate supply unit supplying dialysate to the hemodialyzer and collecting effluent that is used.

To describe the operation of the blood dialyzing apparatus, when the cylinder of the dialysate pump and the effluent pump is expanded, the internal pressure of the cylinder may be reduced, allowing dialysate of the dialysate tank to flow into the cylinder of the dialysate pump and allowing effluent of the hemodialyzer to flow into the cylinder of the effluent pump. In this case, since the dialysate outflow tube is blocked by the first flow-blocking valve, dialysate does not counter flow from the hemodialyzer to the dialysate pump. Likewise, since the effluent outflow tube is blocked by the second flow-blocking valve, effluent of the effluent tank does not counter flow to the effluent pump. In this case, since the dialysate outflow tube is blocked by the first flow-blocking valve, the pressure of the dialysate flow region is lowered compared to the pressure of the blood flow region, and thus a filtration in which water and uremic toxin in blood move to the dialysate region occurs.

On the other hand, when the dialysate pump and the effluent pump are compressed, dialysate of the dialysate pump cylinder is supplied to the hemodialyzer, and effluent of the effluent pump cylinder is discharged to the effluent tank. In this case, since the effluent inflow tube is blocked by the first flow-blocking valve, effluent may not counter flow to the hemodialyzer. Also, since the dialysate inflow tube is blocked by the second flow-blocking valve, dialysate may not counter flow to the dialysate tank. In this case, since the effluent inflow tube is blocked by the first flow-blocking valve, the pressure of the dialysate flow region increases compared to the pressure of the blood flow region, and thus a backfiltration in which water moves from the dialysate region to the blood region occurs.

The blood dialyzing apparatus may further include an auxiliary effluent outflow tube connecting between the effluent inflow tube and the effluent outflow tube and an auxiliary effluent pump disposed on the auxiliary effluent outflow tube to additionally pull effluent of the hemodialyzer toward the effluent tank.

BRIEF DESCRIPTION OF THE DRAWINGS

The accompanying drawings are included to provide a further understanding of the present invention, and are incorporated in and constitute a part of this specification. The drawings illustrate exemplary embodiments of the present invention and, together with the description, serve to explain principles of the present invention. In the drawings:

FIG. 9 is a view illustrating a flow control valve according to a second embodiment of the present invention;

DETAILED DESCRIPTION OF PREFERRED EMBODIMENTS

Preferred embodiments of the present invention will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art.

Hereinafter, a dialysate supply unit and a blood dialyzing apparatus including the dialysate supply unit according to a first embodiment of the present invention will be described in detail with reference to the accompanying drawings.

Figure 1:
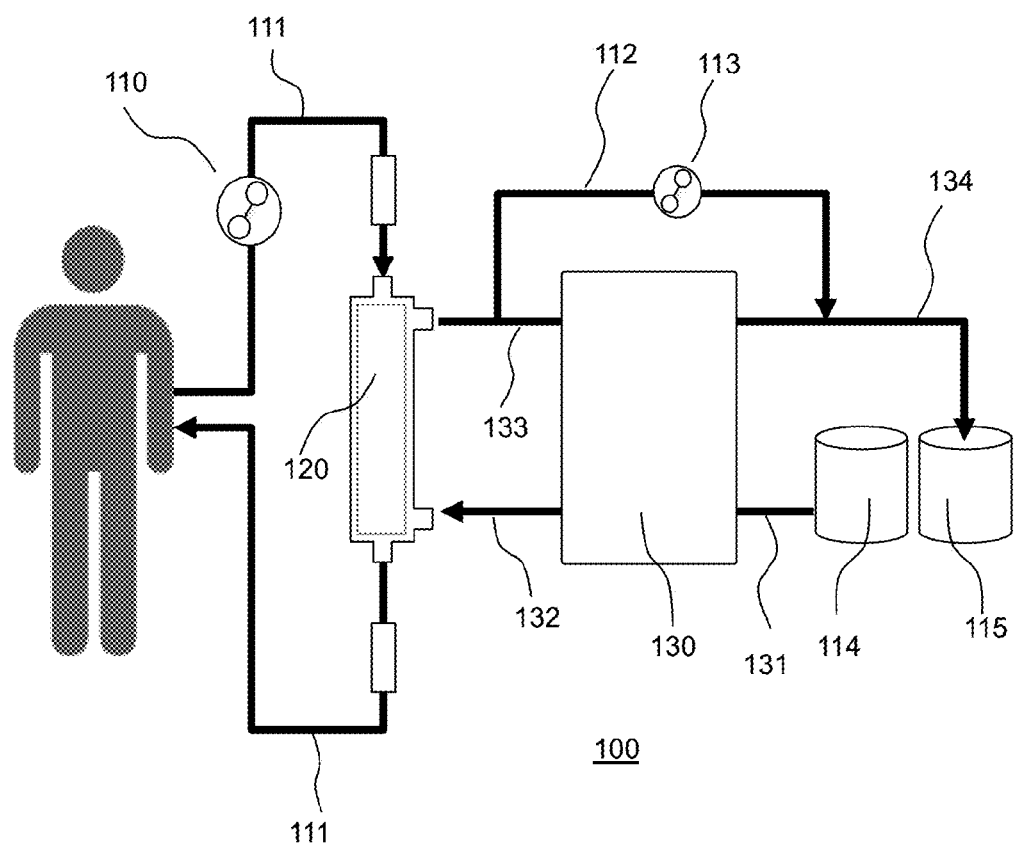
FIG. 1 is a view illustrating a blood dialyzing apparatus according to the present invention.
Figure 2:
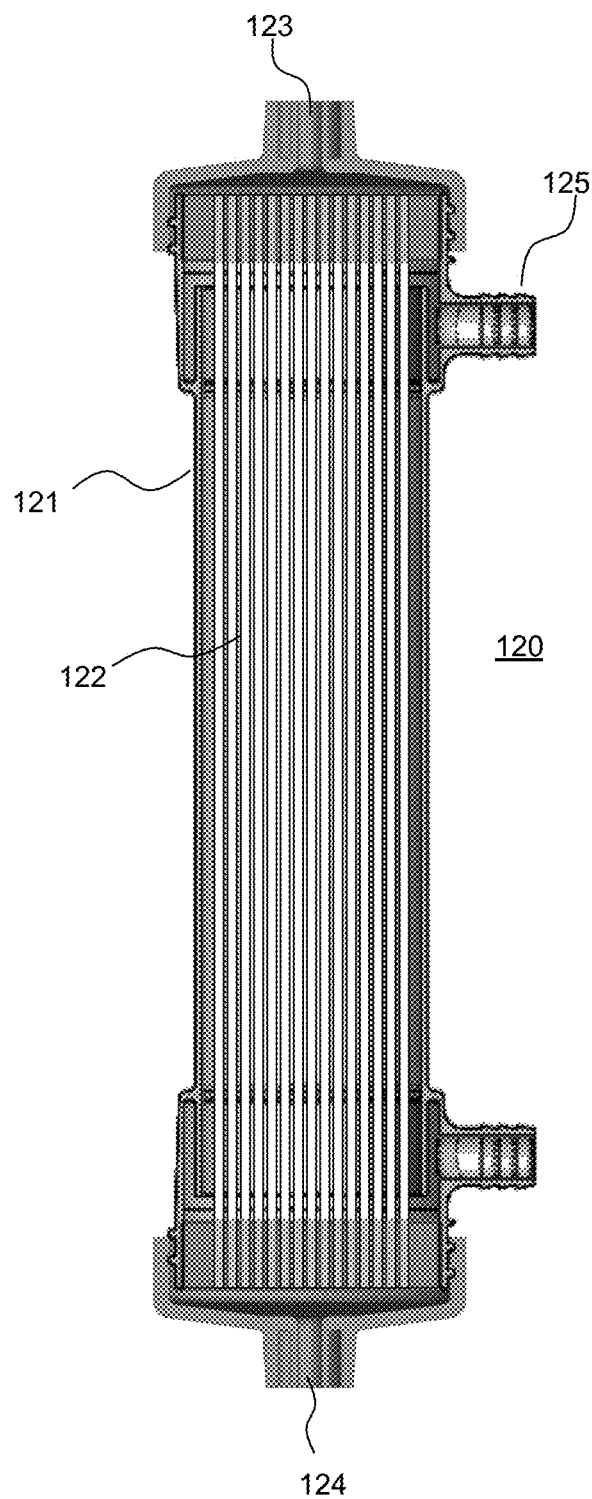
FIG. 2 is a cross-sectional view illustrating a hemodialyzer.

FIG. 1 is a view illustrating a blood dialyzing apparatus according to the present invention, and FIG. 2 is a cross-sectional view illustrating a hemodialyzer. Also, FIG. 3 is a view illustrating a dialysate supply unit according to the first embodiment of the present invention.

As shown in FIG. 1, a blood dialyzing apparatus 100 includes a hemodialyzer 120 in which a mass transfer occurs between blood and dialysate, a blood tube 111 connecting between the hemodialyzer 120 and a patient, a blood pump 110 disposed on the blood tube 111 to transfer blood, a dialysate tank 114 storing dialysate, an effluent tank 115 collecting effluent passing through the hemodialyzer 120, and a dialysate supply unit 130 supplying dialysate to the hemodialyzer 120 and collecting effluent into the effluent tank 115.

As shown in FIG. 2, the hemodialyzer 120 includes a hemodialyzer container 121 having an internal space and a hemodialysis membrane 122 accommodated in the internal space of the hemodialyzer container 121. The internal space of the hemodialyzer container 121 may be divided into a blood flow region and a dialysate flow region by the hemodialysis membrane 122. The hemodialyzer container 121 includes a blood inlet 123 disposed at one end thereof and a blood outlet 124 disposed at the other end thereof. Also, a dialysate inlet 126 and a dialysate outlet 125 may be provided on the outer circumferential surface of the hemodialyzer container 121. Blood passes through the blood flow region inside the hemodialysis membrane 122, and dialysate passes through outside the hemodialysis membrane 122. In this case, blood and dialysate may be desirably configured to flow in the opposite directions to each other.

Figure 3:
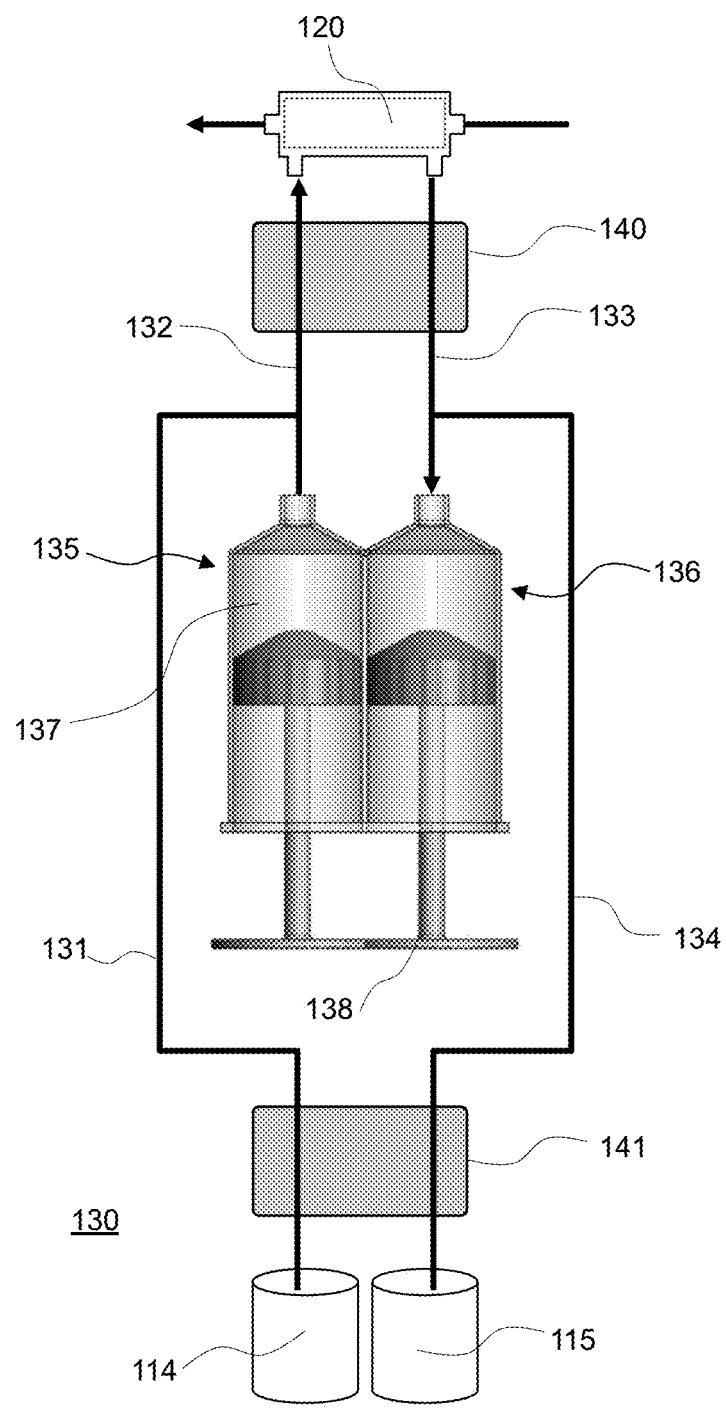
FIG. 3 is a view illustrating a dialysate supply unit according to a first embodiment of the present invention.

As shown in FIG. 3, the dialysate supply unit 130 according to the first embodiment of the present invention may include a dialysate pump 135 connected to the dialysate tank 114 and the hemodialyzer 120 through a dialysate inflow tube 131 and a dialysate outflow tube 132, respectively, an effluent pump 136 connected to the hemodialyzer 120 and the effluent tank 115 through an effluent inflow tube 133 and an effluent outflow tube 134, respectively, a first flow-blocking valve 140 alternately blocking the dialysate outflow tube 132 and the effluent inflow tube 133, and a second flow-blocking valve 141 alternately blocking the dialysate inflow tube 131 and the effluent outflow tube 134. The dialysate pump 135 and the effluent pump 136 may include a cylinder 137 having an internal space, a piston 138 reciprocally disposed inside the cylinder 137, and a piston driver allowing the piston 138 to reciprocate. The piston driver may include various structures that can compress or expand the dialysate pump and the effluent pump cylinders 137 by pushing or pulling the piston 138. The cylinders of the dialysate pump 135 and the effluent pump 136 are simultaneously compressed or expanded.

Figure 4:
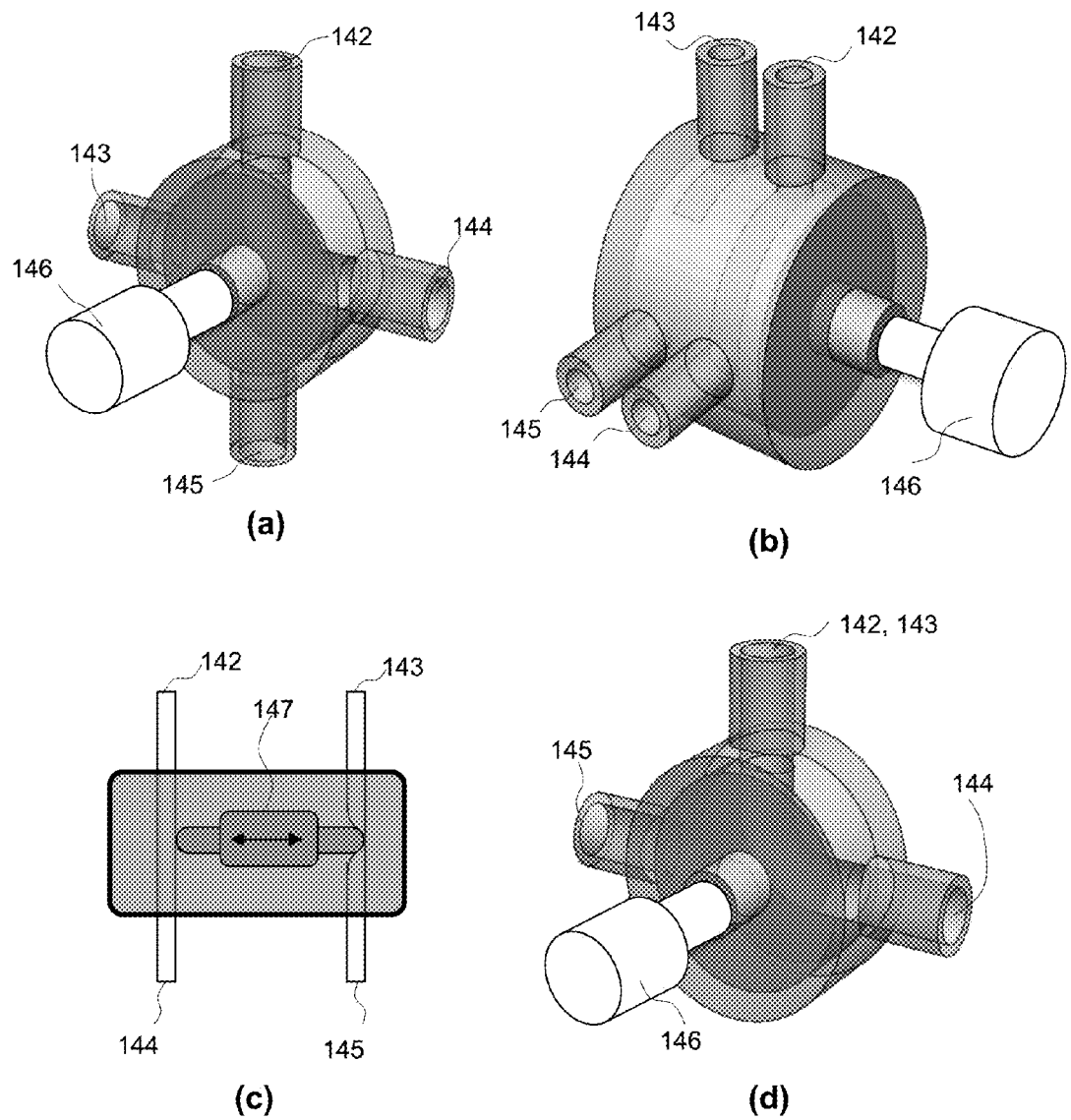
FIG. 4 is a view illustrating a flow-blocking valve according to a first embodiment of the present invention.

The flow-blocking valve 140 or 141 may include various structures that can open and close the dialysate flow passage. As shown in FIGS. 4A and 4B, the flow-blocking valves 140 and 141 may include first to fourth flow ports 142 to 145 and a flow-blocking valve driver 146 for driving the flow-blocking valve 140 or 141. When a flow passage is connected between two flow ports among the four flow ports 142 to 145, the flow-blocking valve driver 146 blocks a flow passage connecting between other two flow ports. FIG. 4C illustrates another exemplary flow-blocking valve. Here, the flow-blocking valve includes a flow-blocking pressurizing member 147 reciprocating in a straight line and a pressurizing member driver providing a straight force to the flow-blocking pressurizing member 147. When the flow-blocking pressurizing member 147 moves to a tube connecting the two flow ports 142 and 144, one end of the flow-blocking pressurizing member 147 compresses a tube supported by a support wall, blocking the flow passage inside the tube. On the other hand, the flow-blocking pressurizing member 147 moves to a tube connecting the other two ports 143 and 145, the other end of the flow-blocking pressurizing member 147 compresses the tube supported by the support wall, blocking the dialysate flow passage inside the tube.

For example, in case of the first flow-blocking valve 140, two flow ports may be connected to the hemodialyzer 120, and the other two flow ports may be connected to the dialysate pump 135 and the effluent pump 136, respectively. In case of the second flow-blocking valve 141, the four flow ports 142 to 145 may be connected to the dialysate pump 135, the effluent pump 136, the dialysate tank 114, and the effluent tank 115, respectively. Also, as shown in FIG. 4D, in case of the first flow-blocking valve 140, one flow port may be connected to the hemodialyzer 120, and the inflow and outflow of dialysate may be performed through the flow port.

The blocking of the dialysate outflow tube 132 by the first flow-blocking valve 140 and the blocking of the effluent outflow tube 134 by the second flow-blocking valve 141 occurs simultaneously. Similarly, the blocking of the effluent inflow tube 133 by the first flow-blocking valve 140 and the blocking of the dialysate inflow tube 131 by the second flow-blocking valve 141 occurs simultaneously. The structure of the flow-blocking valve is not limited to that shown in the drawing, and may be modified into another structure that can alternately block the dialysate outflow tube 132 and the effluent inflow tube 133 or the dialysate inflow tube 131 and the effluent outflow tube 134.

Figure 7:
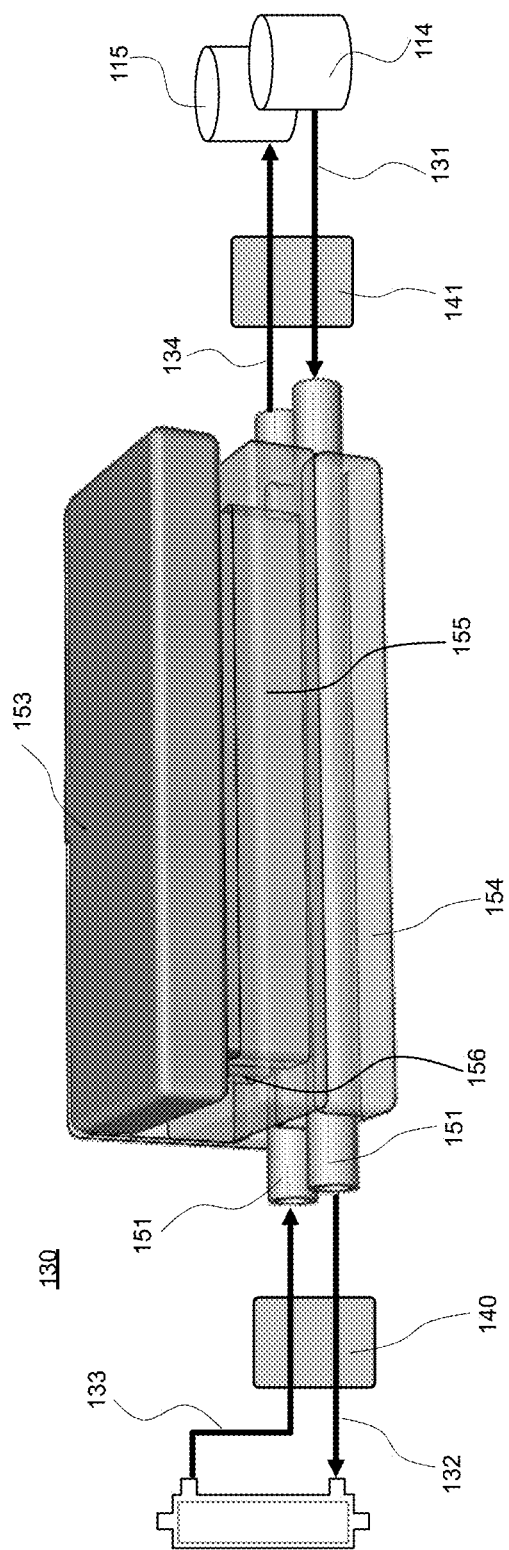
FIG. 7 is a view illustrating another configuration of a dialysate supply unit according to a first embodiment of the present invention.

As shown in FIG. 3, the dialysate pump 135 and the effluent pump 136 may not only include the cylinder 137, the piston 138 reciprocally disposed inside the cylinder 137, and the piston driver allowing the piston 138 to reciprocate, but may also be modified into various structure that can allow dialysate and effluent to flow. For example, as shown in FIG. 7, the cylinder 137 of the dialysate pump 135 and the effluent pump 136 may be modified into a tube 151 formed of a flexible material that can contract and relax. In this case, the piston 138 and the piston driver may be modified into a tube pressurizing member 153 and a pressurizing member driver which can compress and expand the tube 151. The tube pressurizing member 153 pressurizes or expands the tube 151 while rectilinearly moving along a guide rail disposed on one side wall of the dialysate supply unit. The tube pressurizing member 153 may include a pressurizing part 155 protruding to pressurize the tube 151.

The tube pressurizing member driver may include various structures that can apply a reciprocating movement force to the tube pressurizing member 153. An exemplary tube pressurizing member driver may include a cam for pressurizing the tube pressurizing member 153 to a tube support wall 154 and a motor for rotating the cam. When the tube pressurizing member 153 descends toward the tube support wall 154 due to the rotation of the cam, the tube 151 of the dialysate pump and the effluent pump may be simultaneously compressed. When an external force by the cam is removed, the tube pressurizing member 153 may move to the original location, and the tube 151 may be restored to the original state by its own elastic force, expanding the inside of the tube 151. The tube pressurizing apparatus is not limited to the structure shown in the drawing, and may be modified into various structures that can compress and expand the tube 151 of the dialysate pump and the effluent pump. Also, the pressurizing member driver may be modified into another structure that can operate the tube pressurizing member 153.

Hereinafter, the operation of the dialysate supply unit 130 and the blood dialyzing apparatus 100 including the dialysate supply unit 130 according to the first embodiment of the present invention will be described in detail with reference to the accompanying drawings.

Due to the operation of the blood pump 110, blood in the human body passes the hemodialyzer 120, and due to the operation of the dialysate supply unit 130, dialysate is supplied to the hemodialyzer 120 and then collected in the effluent.

Figure 5:
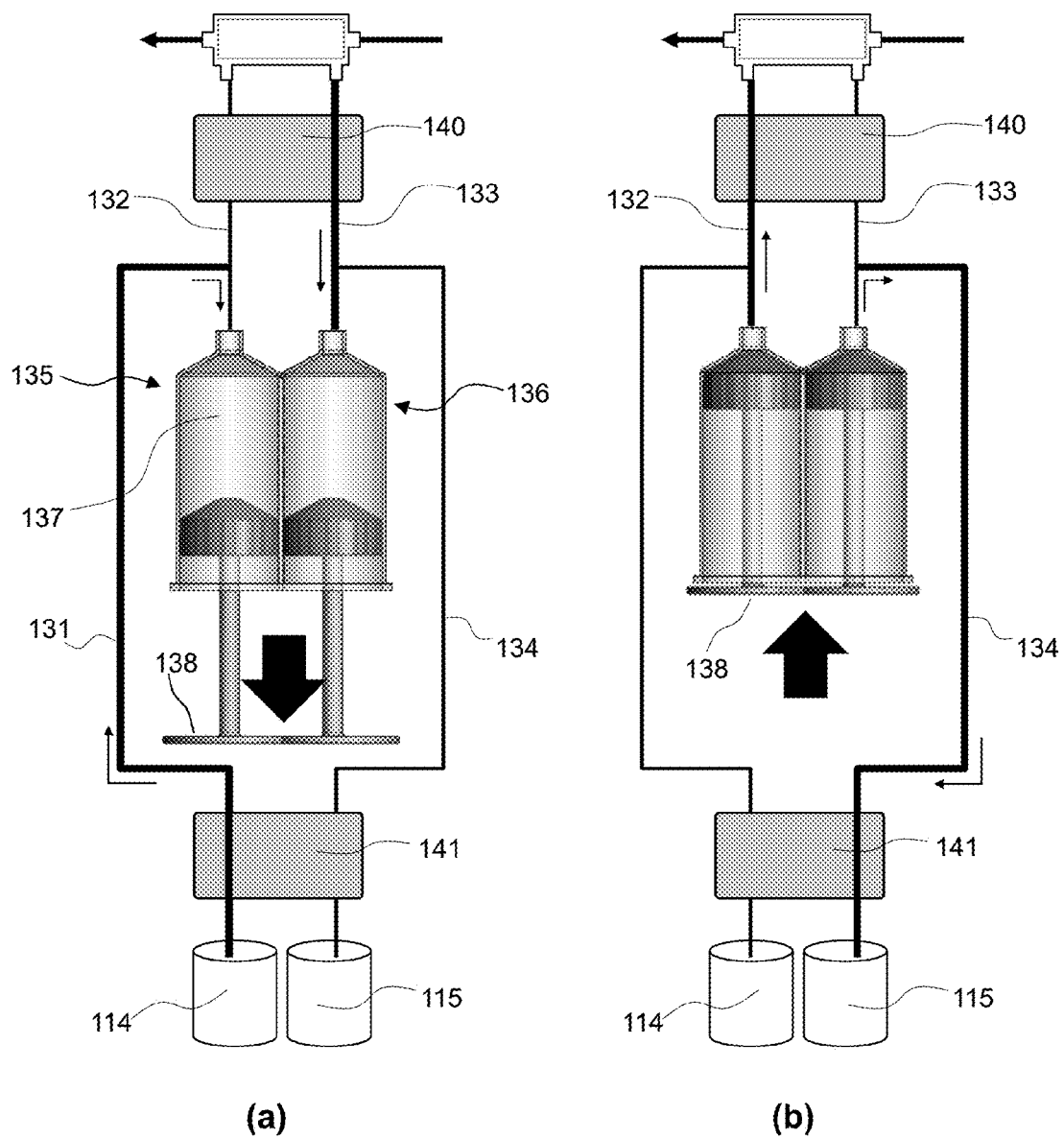
FIG. 5 is a view illustrating the flow of dialysate and effluent when a dialysate and effluent pump cylinder is expanded or compressed in a dialysate supply unit according to a first embodiment of the present invention.

As shown in FIG. 5A, when the cylinder 137 of the dialysate pump 135 and the effluent pump 136 is expanded, the first flow-blocking valve 140 opens the effluent inflow tube 133 and blocks the dialysate outflow tube 132, and the second flow-blocking valve 141 opens the dialysate inflow tube 131 and blocks the effluent outflow tube 134. Due to the expansion of the cylinder of the dialysate pump 135, the internal pressure of the cylinder is reduced, and dialysate of the dialysate tank 114 flows into the cylinder of the dialysate pump 135. In this case, since the dialysate outflow tube 132 is blocked by the first flow-blocking valve 140, dialysate does not counter flow from the hemodialyzer 120 to the dialysate pump 135. Similarly, due to the expansion of the cylinder of the effluent pump 136, effluent of the hemodialyzer 120 flows into the cylinder of the effluent pump 136. In this case, since the effluent outflow tube 134 is blocked by the second flow-blocking valve 141, effluent of the effluent tank 115 does not counter flow to the effluent pump 136. Here, since the dialysate outflow tube 132 is blocked by the first flow-blocking valve 140, the hydrostatic pressure of the dialysate flow region is lowered compared to the hydrostatic pressure of the blood flow region, and thus a filtration in which water and uremic toxin in blood move to the dialysate flow region occurs.

On the other hand, as shown in FIG. 5B, when the cylinder 137 of the dialysate pump 135 and the effluent pump 136 is compressed, the first flow-blocking valve 140 opens the dialysate outflow tube 132 and blocks the effluent inflow tube 133, and the second flow-blocking valve 141 opens the effluent outflow tube 134 and blocks the dialysate inflow tube 131. Due to the compression of the cylinder of the effluent pump 136, effluent inside the cylinder flows into the effluent tank 115. In this case, since the effluent inflow tube 133 is blocked by the first flow-blocking valve 140, effluent does not counter flow to the hemodialyzer 120. Similarly, when the cylinder of the dialysate pump 135 is compressed, dialysate inside the cylinder is supplied to the hemodialyzer 120. In this case, since the dialysate inflow tube 131 is blocked by the second flow-blocking valve 141, dialysate in the dialysate pump cylinder does not counter flow to the dialysate tank 114. At the same time, since the effluent inflow tube 133 is blocked by the first flow-blocking valve 140, the hydrostatic pressure of the dialysate flow region inside the hemodialyzer 120 increases compared to the hydrostatic pressure of the blood flow region, and thus a backfiltration in which water moves from the dialysate flow region to the blood flow region occurs.

When the dialysate and effluent pumps 135 and 136 expand, the Transmembrane Pressure (TMP) that is defined as a difference between mean blood and dialysate pressures in the hemodialyzer 120 becomes a positive (+) value, and the filtration occurs. On the contrary, when the dialysate and effluent pumps 135 and 136 are compressed, TMP becomes a negative (−) value, and the backfiltration occurs. TMP can be expressed as Equation (1).

$$TMP=0.5\times\{(PBi+PBo)-(PDi+PDo)-\pi\} \quad (1)$$

where, $\pi$, PBi, PBo, PDi, and PDo denote blood osmotic pressure, blood inlet pressure, blood outlet pressure, dialysate inlet pressure, and dialysate outlet pressure, respectively.

Figure 6:
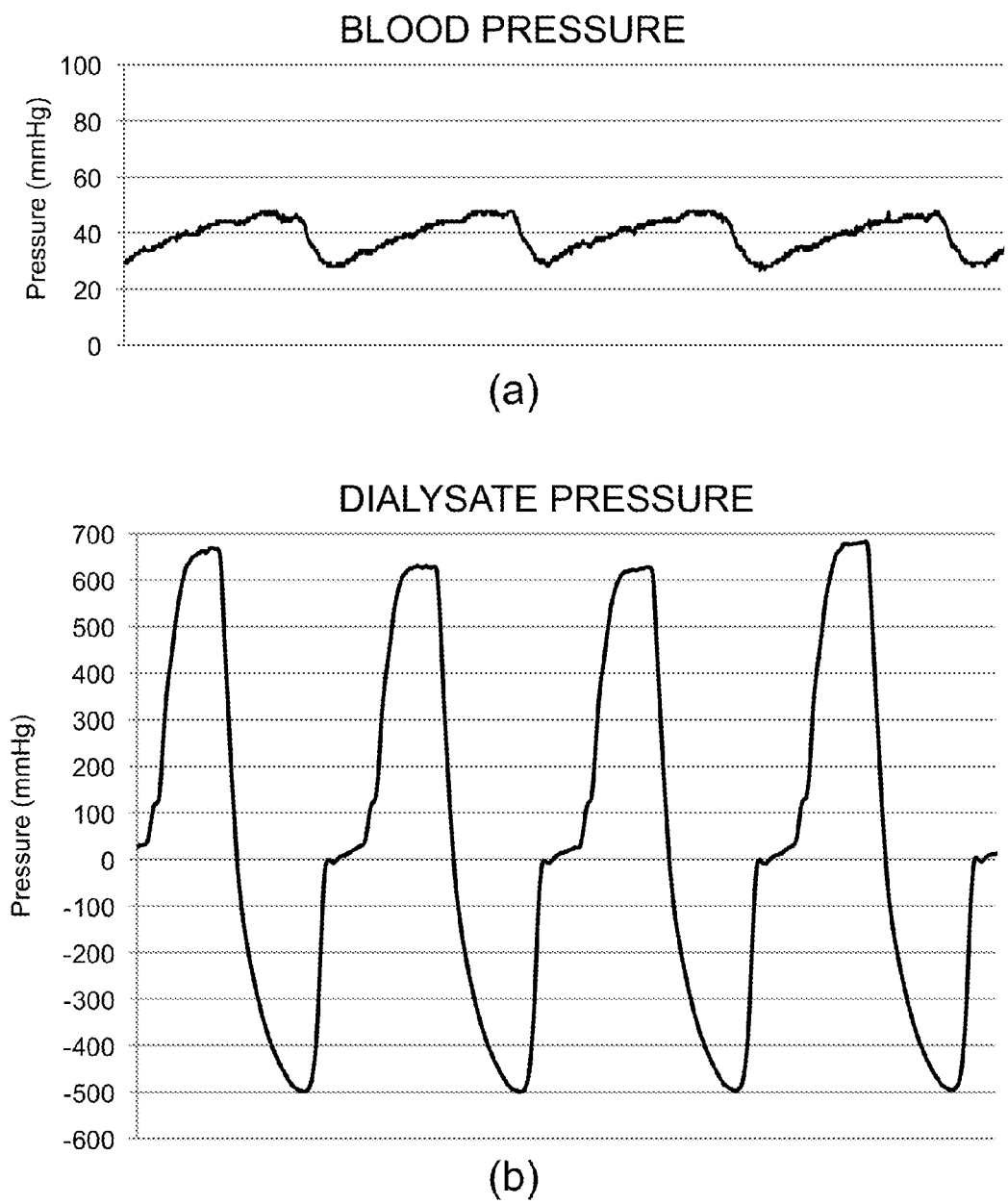
FIGS. 6A and 6B are views illustrating waveforms of a blood pressure and a dialysate pressure caused by a dialysate supply unit of the present invention.

The compression and expansion of the dialysate pump 135 and the effluent pump 136 configures a cycle of filtration and backfiltration. In the dialysis using the dialysate supply unit 130 according to the embodiment of the present invention, the cycle of filtration and backfiltration is continuously repeated, removing water and waste products during the filtration and supplementing lost water during the backfiltration. During the hemodialysis, blood is mainly transferred by a tube squeezing type of roller pump or peristaltic pump. In this case, the blood pressure, as shown in FIG. 6A, shows a slight fluctuation due to the repetition of compression and refilling of the blood tube. However, as shown in FIG. 6B, the dialysate pressure and flow rate caused by the dialysate supply unit shows a significantly remarkable fluctuation compared to the blood pressure. This is because the fluid movement by the compression and expansion of the cylinder according to the embodiment of the present invention causes a significantly remarkable pulsatile flow compared to the roller pump or peristaltic pump which transfers fluid by compressing the blood tube. Accordingly, since the fluctuation of the blood pressure is significantly smaller than the fluctuation of the dialysate pressure, the blood pressure may be considered as a uniform pressure, and due to the remarkable fluctuation of the dialysate pressure, TMP alternately repeats a positive (+) value and a negative (−) value.

Here, a compression and expansion cycle (frequency, cycle/min) of the dialysate pump 135 and the effluent pump 136 may be appropriately controlled according to the prescription of the dialysate flow rate that is needed in the hemodialysis treatment. That is, the dialysate flow rate (Qd) by the dialysate pump 135 and the effluent collection rate by the effluent pump 136 may be expressed as Equation (2) using the compression-expansion volume (V) and the cylinder compression-expansion cycle (F).

$$Qd \text{ [ml/min]}=V \text{ [ml/cycle]}\times F \text{ [cycle/min]} \quad (2)$$

For example, in the hemodialysis treatment, assuming that the blood flow rate (QB) of a patient is about 200 to 250 ml/min and the dialysate flow rate is about 600 ml/min for about 4-hour treatment, when the internal compress-expansion volume of the cylinder 137 of the dialysate pump and the effluent pump is about 20 ml, the dialysate and effluent pump 135 and 136 according to the embodiment need compression-expansion of 30 cycles per minute. V may be determined by the inner diameter of the cylinder and the transfer distance (d) per cycle of the piston, and F may be determined by Qd and V that are needed.

Here, the dialysate pump 135 and the effluent pump 136 may transfer the same amount of dialysate and effluent. That is, since the cylinder 137 of the dialysate pump 135 and the effluent pump 136 simultaneously repeats the compression and expansion by the same piston driver, the supply amount to the hemodialyzer 120 by the dialysate pump 135 and the discharge amount out of the hemodialyzer 120 may be equal to each other.

However, in an actual hemodialysis, blood cells and plasma proteins in blood may adhere to the inner wall of the hemodialysis membrane, hindering the water movement from the blood region to the dialysate region. Accordingly, for the occurrence of the same amount of filtration and backfiltration, a greater positive (+) TMP for the filtration may be needed compared to a negative (−) TMP for the backfiltration. In order to transfer the same amount of dialysate and effluent by the dialysate pump 135 and the effluent pump 136, a longer time may be assigned to the filtration compared to the backfiltration, or the volume of the cylinder of the effluent pump 136 may be designed to be greater than the volume of the cylinder of the dialysate pump 135. Alternately, the supply amount of dialysate by the dialysate pump 135 and the collection amount of effluent by the effluent pump 136 may be appropriately controlled by adjusting the transfer distance (d) of the pistons of the dialysate pump 135 and the effluent pump 136.

Also, since water is accumulated in the body of a patient with renal disease due to the absence of the kidney function, it is important to remove excess water from the body as well as remove waste product from the body upon hemodialysis. For this, as shown in FIG. 1, an auxiliary effluent outflow tube 112 may connect between the effluent inflow tube 133 and the effluent tank 115 or between the effluent inflow tube 133 and the effluent outflow tube 134. Also, an auxiliary effluent pump 113 may be disposed on the auxiliary effluent outflow tube 112 to additionally pull effluent of the hemodialyzer 120 toward the effluent tank 115. In a situation where the supply amount and the discharge amount of dialysate by the dialysate supply unit 130 are equal to each other, when the auxiliary effluent pump 113 operates, water may be additionally discharged out of blood, thereby removing excess water accumulated in the body of a patient.

Hereinafter, a dialysate supply unit according to a second embodiment of the present invention will be described in detail with reference to the accompanying drawings.

Figure 8:
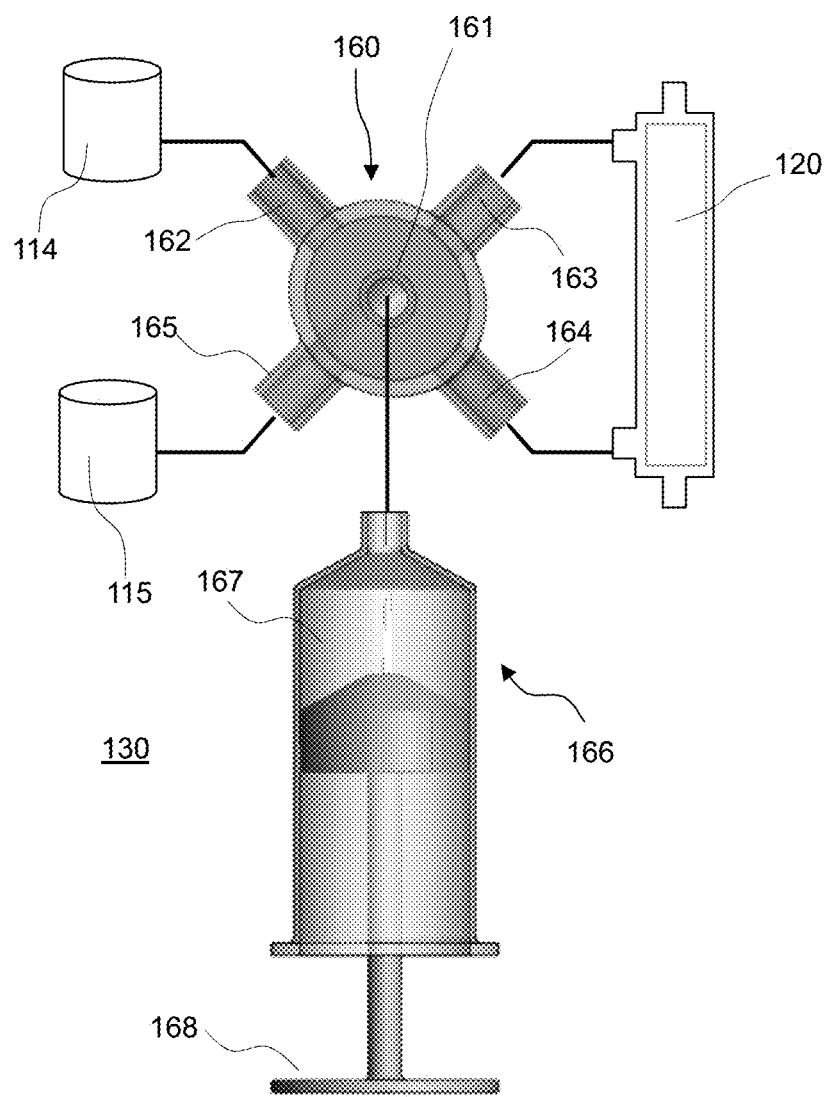
FIG. 8 is a view illustrating a dialysate supply unit according to a second embodiment of the present invention.

FIG. 8 is a view illustrating a dialysate supply unit 130 according to a second embodiment of the present invention. FIGS. 9A and 9B are views illustrating a flow control valve 160 according to a second embodiment of the present invention. FIGS. 10A to 10D are views illustrating an operational mechanism of a dialysate supply unit according to a second embodiment of the present invention.

As shown in FIG. 8, a dialysate supply unit 130 according to a second embodiment of the present invention may include a dialysate pump 166 supplying dialysate of a dialysate tank 114 to a hemodialyzer 120 and collecting used dialysate, i.e., effluent, from the hemodialyzer 120, a flow control valve 160 sequentially controlling flow passages between the dialysate pump 166 and the dialysate tank 114, between the dialysate pump 166 and the hemodialyzer 120, and between the dialysate pump 166 and an effluent tank 115, and a flow control valve driver for driving the flow control valve 160. The dialysate pump 166 may include a cylinder 167 having an internal space, a piston 168 reciprocally disposed inside the cylinder 167, and a piston driver allowing the piston 168 to reciprocate.

The flow control valve 160 may include various structures that sequentially connect flow passages between the dialysate pump 166 and the dialysate tank 114, between the dialysate pump 166 and the hemodialyzer 120, and between the dialysate pump 166 and an effluent tank 115. For example, as shown in FIGS. 9A and 9B, the flow control valve 160 may include a pump port 161 connected to the dialysate pump 166, a first dialysate port 162 connected to the dialysate tank 114, a second dialysate port 163 connected to the hemodialyzer 120, a first effluent port 164 connected to the hemodialyzer 120, and a second effluent port 165 connected to the effluent tank 115. When a dialysate flow passage between the pump port 161 and one of the four ports except the pump port 161 is opened, the flow of dialysate through other three ports may be temporarily blocked.

However, as shown in FIGS. 9A and 9B, there is a difference in flow passage connection structure between the pump port 161 and the other four dialysate and effluent ports 162 to 165. In FIG. 9A, the connection passages between the pump port 161 and the dialysate and effluent ports 162 to 165 connected thereto may have a pipe shape, but in FIG. 9B, the connection passages may have a fan shape. Without being limited to the structures shown in FIGS. 9A and 9B, the structure of the flow control valve 160 may be modified into other structures that sequentially connect the flow passages between the dialysate pump 166 and the dialysate tank 114, between the dialysate pump 166 and the hemodialyzer 120, and between the dialysate pump 166 and an effluent tank 115.

Hereinafter, the operation of the dialysate supply unit 130 and the blood dialyzing apparatus 100 including the dialysate supply unit 130 according to the second embodiment of the present invention will be described in detail with reference to the accompanying drawings.

Due to the operation of the blood pump 110, blood in the human body passes the hemodialyzer 120, and due to the operation of the dialysate pump 166, dialysate of the dialysate tank 114 is supplied to the hemodialyzer 120 and then collected in the effluent tank.

Figure 10:
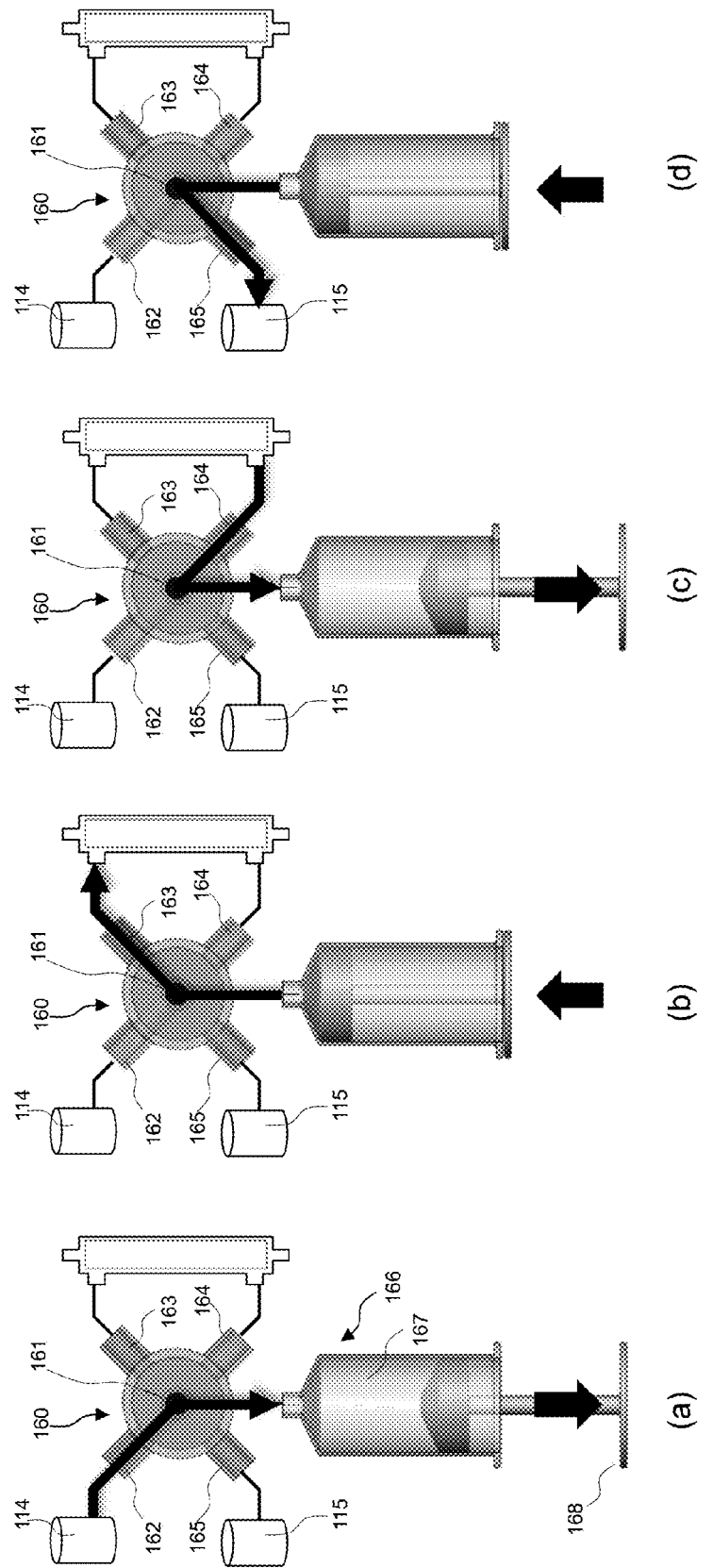
FIG. 10 is a view illustrating an operational mechanism of a dialysate supply unit according to a second embodiment of the present invention.

The dialysate transfer according to the second embodiment of the present invention may include a first step of connecting a flow passage between the dialysate pump 166 and the dialysate tank 114 by the flow control value 160 and allowing dialysate of the dialysate tank 114 to flow into the cylinder 167 by expanding the cylinder 167 of the dialysate pump 166 as shown in FIG. 10A, a second step of connecting a flow passage between the dialysate pump 166 and the hemodialyzer 120 and supplying dialysate of the cylinder 167 to the hemodialyzer 120 by compressing the cylinder 167 as shown in FIG. 10B, a third step of connecting a dialysate flow passage between the dialysate pump 166 and the hemodialyzer 120 and allowing dialysate of the hemodialyzer 120, i.e., effluent, to flow into the cylinder 167 by expanding the cylinder 167 as shown in FIG. 10C, and a fourth step of connecting a flow passage between the dialysate pump 166 and the effluent tank 115 and discharging dialysate of the cylinder 167 to the effluent tank 115 by compressing the cylinder of the dialysate pump 166 as shown in FIG. 10D.

Particularly, in the second step, since the first effluent port 164 is blocked by the flow control valve 160 while dialysate is being supplied to the hemodialyzer 120 through the second dialysate port 163, the pressure of the dialysate flow region increases compared to the pressure of the blood flow region, and thus a backfiltration occurs. On the contrary, in the third step, the second dialysate port 163 is blocked by the flow control valve 160. Accordingly, when dialysate is discharged to the cylinder of the dialysate pump 166, the pressure of the dialysate flow region is lowered compared to the pressure of the blood flow region, and thus a filtration occurs. Here, the second dialysate port 163 and the first effluent port 164 can perform roles of two ports with a single port.

Figure 11:
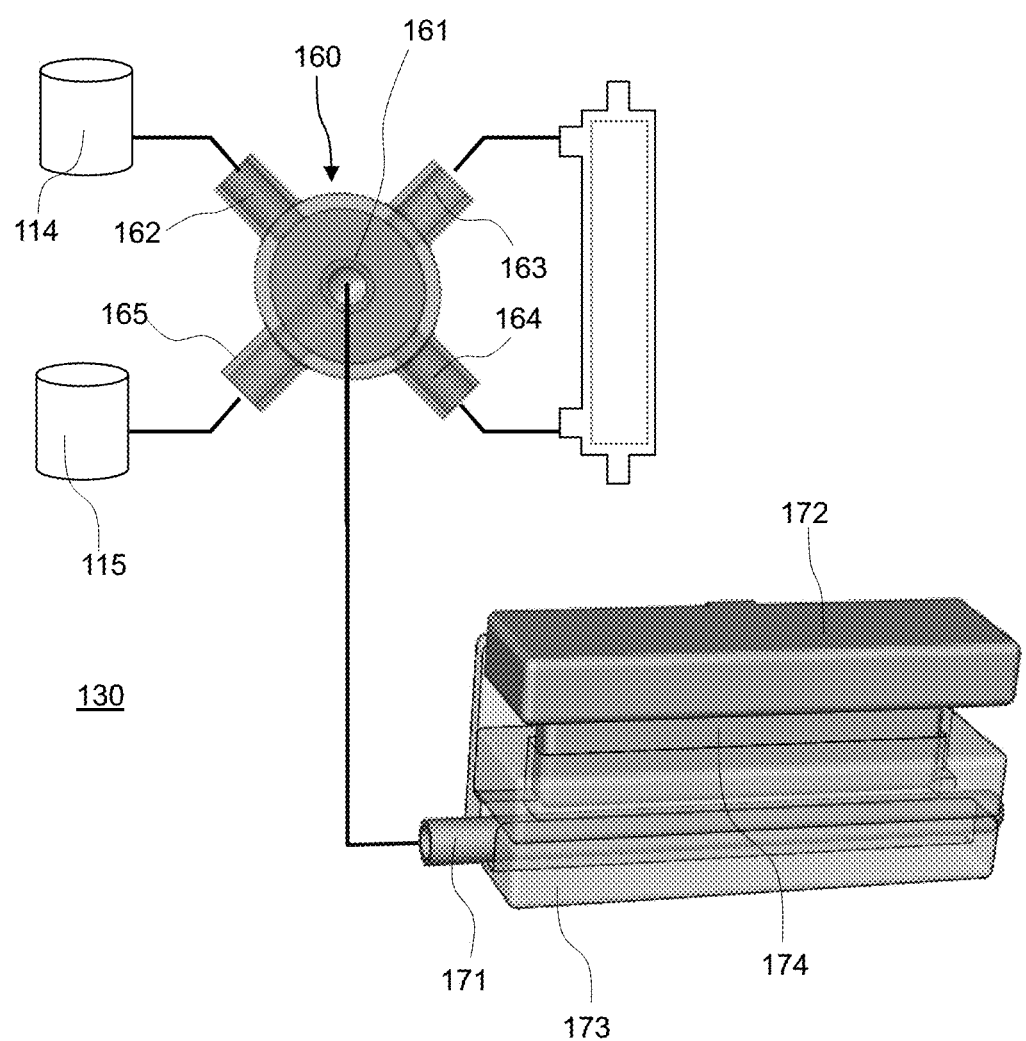
FIG. 11 is a view illustrating another configuration of a dialysate supply unit according to a second embodiment of the present invention.

Here, the dialysate pump 166 may not only include the cylinder 167 having an internal space, the piston 168 reciprocally disposed inside the cylinder 167, and the piston driver allowing the piston 168 to reciprocate, but may also be modified into various structures that can transfer dialysate. For example, as shown in FIG. 11, the cylinder 167 of the dialysate pump 166 may be modified into a tube 171 formed of a flexible material that can contract and relax. In this case, the piston 168 and the piston driver may be modified into a tube pressurizing member 172 and a pressurizing member driver which can pressurize and expand the tube 171. The tube pressurizing member 172 compresses or expands the tube 171 while rectilinearly moving along a guide rail disposed on one side wall of the dialysis supply unit, and may include a pressurizing part 174 to pressurize the tube 171. The tube pressurizing apparatus is not limited to the structure shown in the drawing, and may be modified into various structures that can compress and expand the tube 171. Also, the pressurizing member driver may be modified into various structures that can apply a reciprocating movement force to the tube pressurizing member 172.

Thus, the blood dialyzing apparatuses 100 according to the embodiments can quickly and significantly change the dialysate pressure inside the hemodialyzer 120 using the dialysate supply unit 130, including the cylinders 137 and 167 and the pistons 138 and 168, or the tubes 151 and 171 and the tube pressurizing members 153 and 172. Accordingly, a pressure difference between blood and dialysate inside the hemodialyzer 120 may repeat a positive (+) value and a negative (−) value, thereby increasing water exchange and mass transfer and improving the hemodialysis efficiency without increasing the size of the hemodialyzer 120 or the flow rate of blood and dialysate.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A dialysate supply unit for supplying dialysate of a dialysate tank to a hemodialyzer and collecting dialysate passing through the hemodialyzer in an effluent tank, the dialysate supply unit comprising:

a dialysate pump connecting the dialysate tank and the hemodialyzer;

an effluent pump connecting the hemodialyzer and the effluent tank;

a first flow-blocking valve alternately blocking a dialysate outflow tube connecting the hemodialyzer and the dialysate pump and an effluent inflow tube connecting the hemodialyzer and the effluent pump;

a second flow-blocking valve alternately blocking a dialysate inflow tube connecting the dialysate pump and the dialysate tank and an effluent outflow tube connecting the effluent pump and the effluent tank; and a flow-blocking valve driver for driving the first flow-blocking valve or the second flow-blocking valve, wherein the dialysate pump and the effluent pump each comprise a cylinder, a piston reciprocally disposed inside the cylinder, and a piston driver allowing the piston to reciprocate, wherein each of the cylinders has one chamber for containing dialysate, and wherein all chambers are directly connected to the hemodialyzer and are simultaneously compressed or expanded.

2. The dialysis supply unit of claim 1, wherein the dialysate outflow tube and the effluent outflow tube are simultaneously blocked or opened, and the effluent inflow tube and the dialysate inflow tube are simultaneously blocked or opened.

3. The dialysis supply unit of claim 2, wherein the first flow-blocking valve and the second flow-blocking valve comprise:
a housing having an internal space;
a flow port disposed on the outer surface of the housing; and
a rotating member disposed inside the housing to connect flow passage between flow ports.

4. The dialysis supply unit of claim 3, wherein the first flow-blocking valve and the second flow-blocking valve further comprise a flow path disposed inside the rotating member.

5. The dialysis supply unit of claim 4, wherein the flow path has an L shape, the L-shaped flow path having a bending portion.

6. The dialysis supply unit of claim 3, wherein a slit is provided in a side wall of the rotating member to connect flow passage between flow ports.

7. The dialysis supply unit of claim 6, wherein the slit has a fan shape extending outwardly from a middle portion of the rotating member.

8. The dialysis supply unit of claim 3, wherein the first flow-blocking valve and the second flow-blocking valve comprise an odd number of flow ports.

9. The dialysis supply unit of claim 1, wherein the dialysate pump and the effluent pump transfer substantially the same amount of dialysate.

10. The dialysis supply unit of claim 1, further comprising:
an auxiliary effluent outflow tube connecting between the effluent inflow tube and the effluent outflow tube; and
an auxiliary effluent pump disposed on the auxiliary effluent outflow tube to pull dialysate of the hemodialyzer.

* * * * *